US00PP16981P2

(12) United States Plant Patent
Lommerse

(10) Patent No.: US PP16,981 P2
(45) Date of Patent: Aug. 15, 2006

(54) ***GAURA LINDHEIMERII* PLANT NAMED 'GAUSUDRE'**

(50) Latin Name: *Gaura lindheimerii*
Varietal Denomination: Gausudre

(76) Inventor: Petrus Ruthgerus Jozef Lommerse, Plantenkwekerij 'Dehulstof, Pilarenlaan 65, 2211 WS Noordwijkerhout (NL)

( * ) Notice: Subject to any disclaimer, the term of this patent is extended or adjusted under 35 U.S.C. 154(b) by 5 days.

(21) Appl. No.: 11/100,367

(22) Filed: Apr. 6, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP13,189 P2 * 11/2002 Bentley ..... Plt./226
PP14,683 P2 * 4/2004 Knosher ..... Plt./226

* cited by examiner

*Primary Examiner*—Kent L. Bell
*Assistant Examiner*—W. C. Haas
(74) *Attorney, Agent, or Firm*—The Webb Law Firm

(57) ABSTRACT

A new and distinct *Gaura lindheimerii* plant with a compact growth habit, large deep rose colored flowers, and a long blooming season.

3 Drawing Sheets

Botanical classification: *Gaura lindheimerii.*
Varietal denomination: 'Gausudre'.

BACKGROUND OF THE INVENTION

The present invention comprises a new and distinct cultivar of *Gaura lindheimerii* known by the varietal name 'Gausudre'. The new variety originated in a planned breeding program in The Netherlands as a result of cross breeding *Gaura* 'Siskyou Pink' (female parent, unpatented) and an unnamed short form *Gaura* (male parent, unpatented). The new variety is more compact and exhibits more free branching and a deeper flower color than both parents, which met the goals of the breeding program. The large and uniformly colored flowers of 'Gausudre' differ from other *Gaura lindheimerii* varieties known to the breeder. The new variety was first asexually reproduced by rooted terminal tip cuttings in The Netherlands. The new variety has been trial and field tested and has been found to retain its distinctive characteristics and remain true to type through successive propagations.

DESCRIPTION OF THE DRAWINGS

The accompanying photographic drawings illustrate the new variety, with the color being as nearly true as is possible with color illustrations of this type.

DESCRIPTION OF THE PLANT

Figure 1:
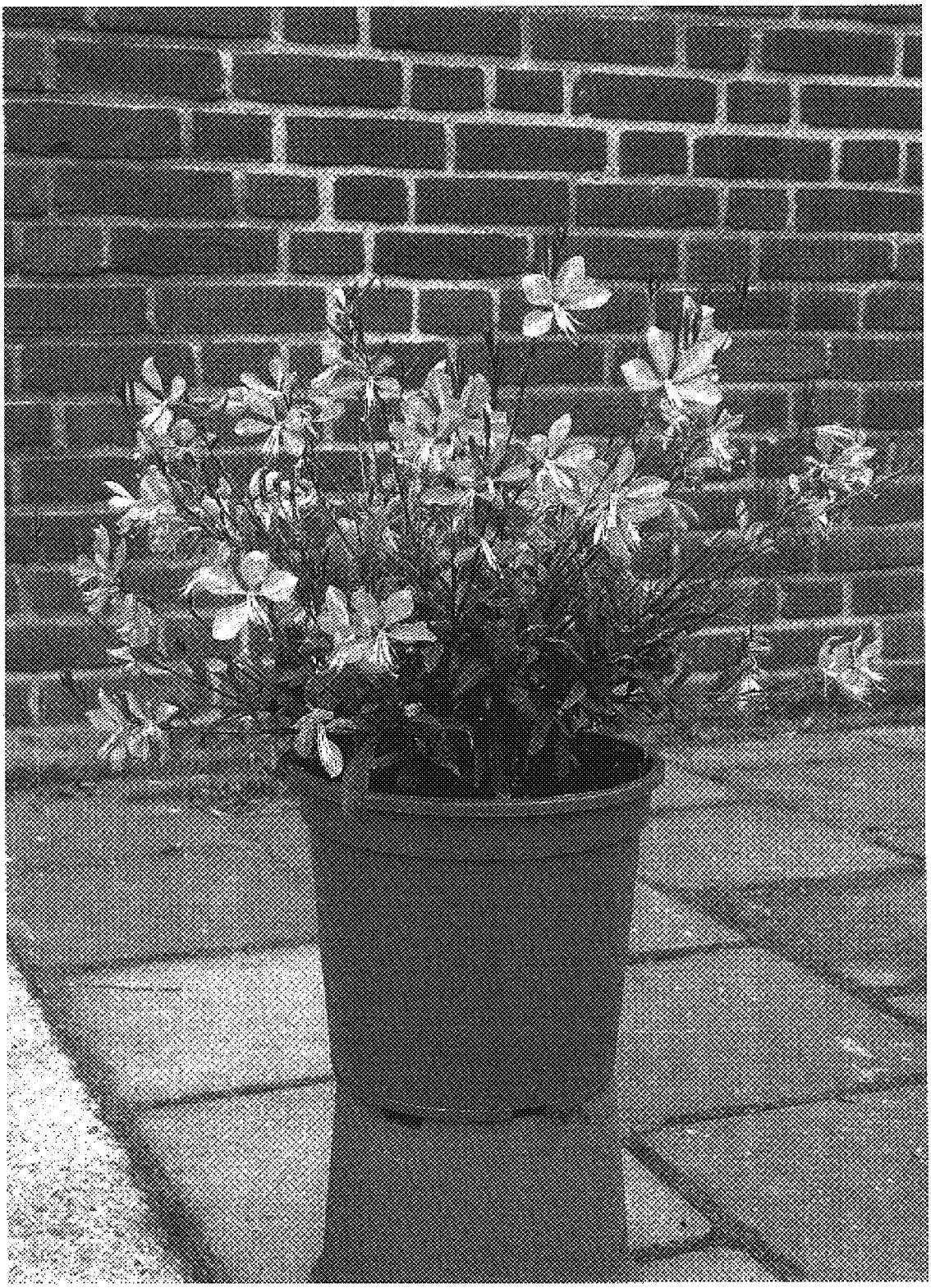
FIG. 1 is a photograph of the new variety.
Figure 2:
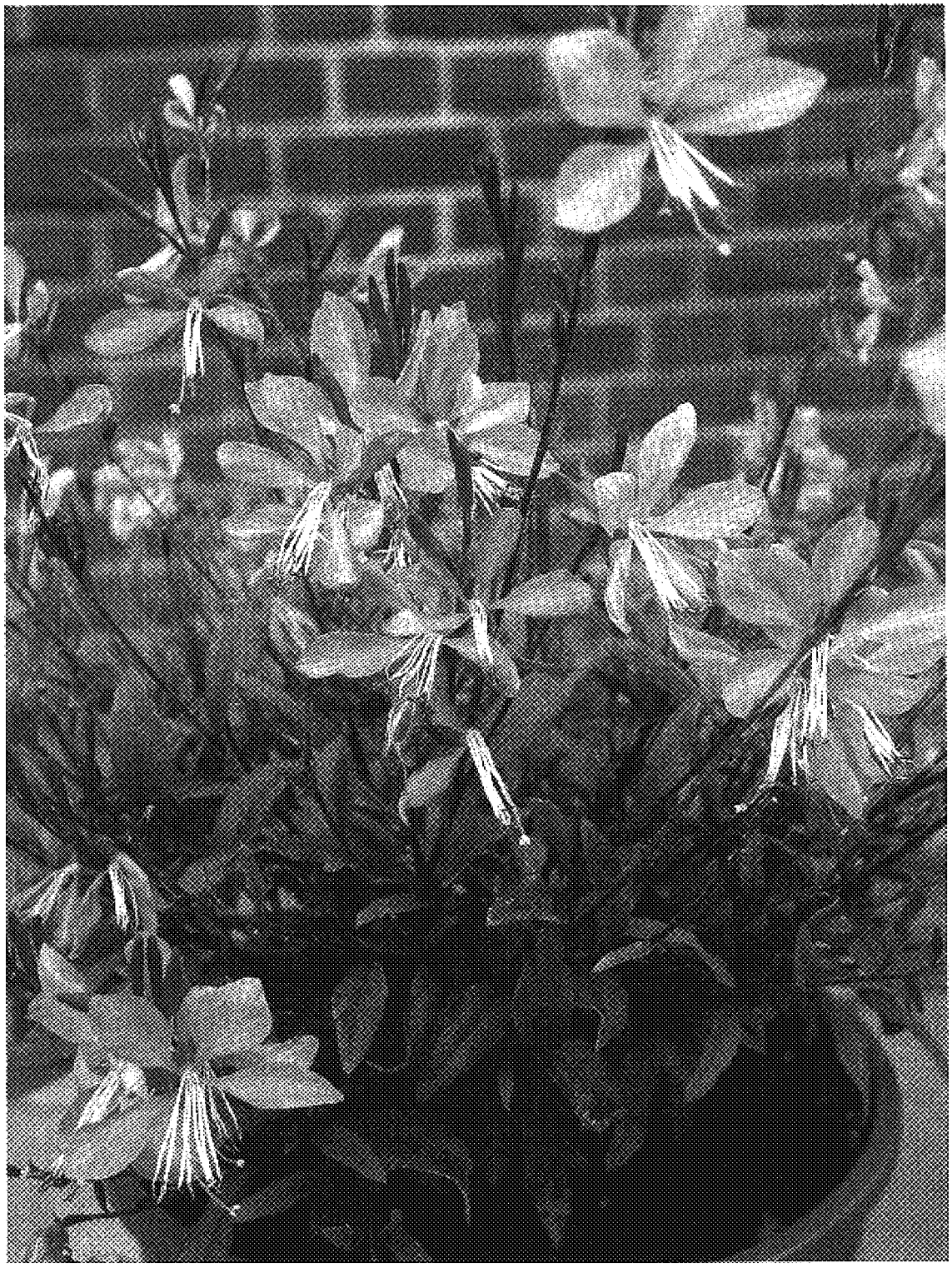
FIG. 2 is a close-up photograph of the new variety.
Figure 3:
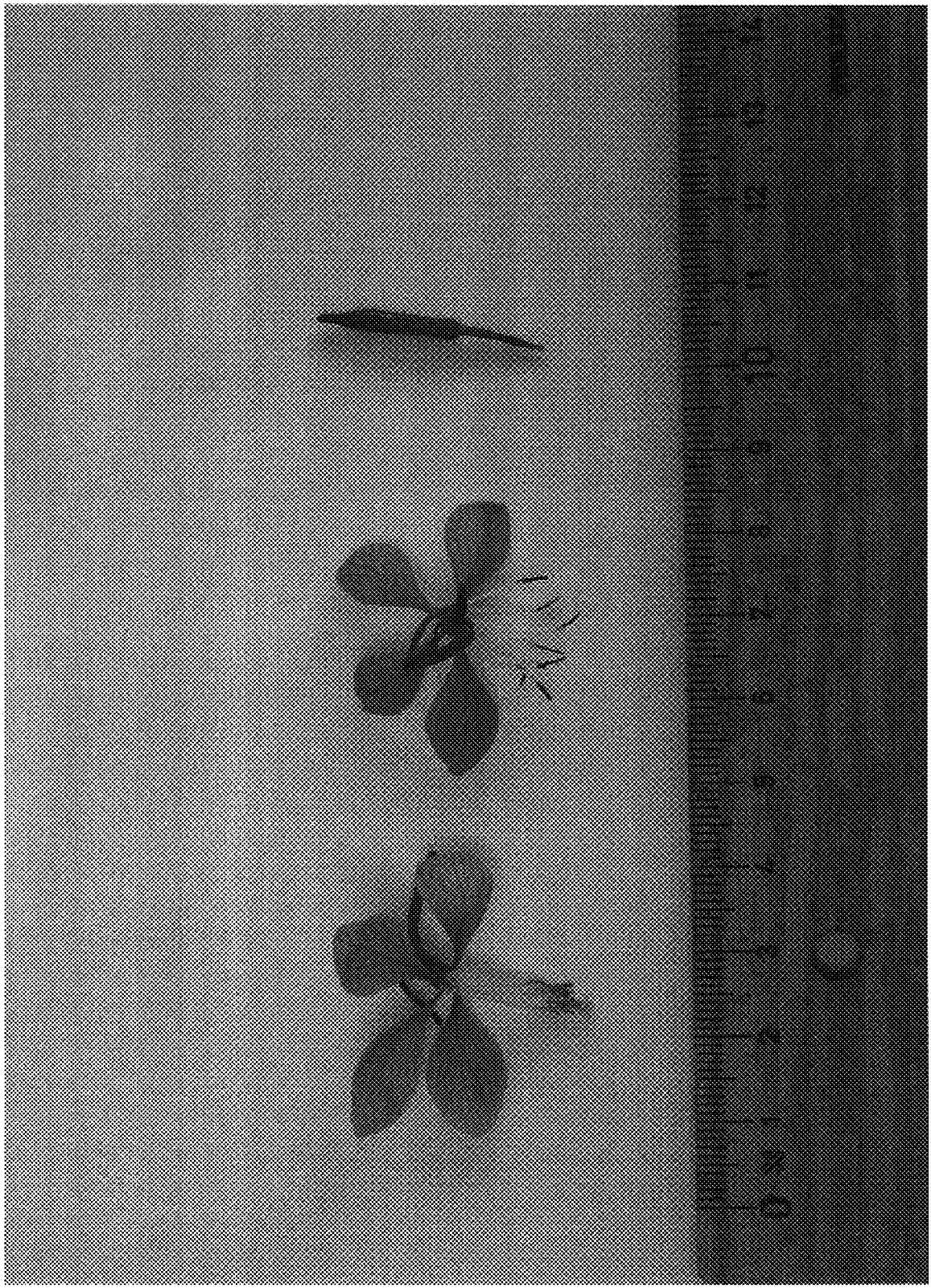
FIG. 3 is a close-up photograph of the flowers of the new variety.

The following detailed description sets forth the characteristics of the new cultivar grown outside in peat-based compost in 17 cm pots with no extra fertilizer in The Netherlands. The data which defines these characteristics was collected by asexual reproductions by cuttings. The color readings were taken in The Netherlands under natural daylight. Color references are primarily to The R.H.S. Colour Chart of The Royal Horticultural Society of London.

PLANT

Time to initiate roots: About 9 days at 21° C.
Time to develop roots: About 28 days at 20° C.
Time to produce a finished flowering plant from a rooted cutting: About 8 weeks in a 9.0 cm container.
Form: Upright and rounded.
Stem:
- *Diameter.*—Average of 3.5 mm.
- *Color.*—145A flushed with 59A.
- *Texture.*—Smooth.
- *Pubescence.*—Light.
- *Form.*—Erect.

Height: Blooms are 35 cm above soil with a stem height of approximately 15 cm when grown in a pot.
Diameter: In a pot, the plant grows to 25 cm in diameter. When grown in the ground, the new variety grows to 35 cm in diameter.
Vigor: Medium.
Branching habit: Free.
Lateral branches:
- *Diameter.*—Average of 2.0 mm.
- *Internode length.*—Average of 1.0 cm.
- *Texture.*—Smooth.
- *Pubescence.*—Light.
- *Color.*—Approximately 59A to 59B with some 145A as the stem matures.

Foliage:
- *Arrangement.*—Single; alternate.
- *Size of leaf.*—Length: 4.2 cm average. Width: 0.9 cm average.
- *Shape of leaf.*—Oblanceolate.
- *Shape of apex.*—Acute.
- *Shape of base.*—Attenuate.
- *Texture.*—Soft.

*Margin type*.—Slightly undulate and entire.
*Pubescence*.—Slight on both upper and lower surfaces.

Color:
*Young leaves*.—Upper surface: 137B to 137C, with a flushing of 59B. Lower surface: 137B to 137C, with a flushing of 59B.
*Mature leaves*.—Upper surface: 146A to 146B, with a light flushing of 59B. Lower surface: 146B to 146C.

Petiole:
*Length*.—Average of 4.0 mm.
*Diameter*.—Average of 2.0 mm.
*Color*.—146B with a flushing of the vein being 59B.

Veins:
*Type*.—Regular.
*Color* (*both surfaces*).—Younger leaves have a 60A color becoming 146B in older leaves.

FLOWER

Bud:
*Stage when bud characteristics determined*.—1 to 2 days prior to opening.
*Shape*.—Linear.
*Diameter*.—2.5 mm average.
*Length*.—19 mm average.
*Color*.—Main body is 60A with the tip color being 59A.

Natural flowering season: Flowering begins in April and continues until the middle of October.

Spike:
*Number of flowers*.—Average 22.
*Length*.—18 cm above foliage.
*Diameter across bloom*.—6.4 cm average.

Corolla:
*Form*.—Zygomorphic.
*Petals/lobes*.—Number: 4. Length: 20 mm average. Width: 11 mm average. Shape: Obovate. Margin: Entire. Texture and appearance: Smooth, matte. Color (when opening): Both surfaces: 61C with veins of 61B. Color (when fully opened): Both surfaces: 61D with veins of 61B to 61C.

Calyx:
*Form*.—Fused at tip.
*Length*.—16 mm average.
*Diameter*.—2.0 mm average.
*Sepal shape*.—Linear.
*Sepal margin*.—Entire.
*Sepal texture*.—Smooth, slightly pubescent.
*Sepal size*.—Length: 16 mm average. Width: 1.5 mm average.
*Sepal color*.—Upper surface: 60A. Lower surface: 60A.

Fragrance: None.
Disease resistance: Good.
Temperature tolerance: Good.
Drought tolerance: Good.
Lasting quality: Flowers last 1–2 days individually.

REPRODUCTIVE ORGANS

Stamens:
*Number*.—8 per flower.
*Filament length*.—11 mm average.
*Anthers*.—Shape: Linear. Length: 3.0 mm. Color: 60A.
*Pollen*.—Color: 3B. Amount: Plentiful.

Pistils:
*Length*.—23 mm average.
*Style*.—Length: 21 mm average. Color: 61C to 61D.
*Stigma*.—Shape: Cruciform. Color: 8D.

Seeds: None produced.

I claim:

1. A new and distinct variety of *Gaura lindheimerii* plant substantially as shown and described.

* * * * *